United States Patent
Parker et al.

(10) Patent No.: US 11,986,245 B2
(45) Date of Patent: May 21, 2024

(54) EVALUATION OF INSTABILITY USING IMAGING AND MODELING FOLLOWING ARTHROPLASTY

(71) Applicant: New York Society for the Relief of the Ruptured and Crippled, maintaining the Special Surgery, New York, NY (US)

(72) Inventors: Christina Esposito Parker, Marrickville (AU); Joseph D. Lipman, New York, NY (US); David J. Mayman, New York, NY (US)

(73) Assignee: NEW YORK SOCIETY FOR THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 754 days.

(21) Appl. No.: 15/734,460

(22) PCT Filed: Jun. 13, 2019

(86) PCT No.: PCT/US2019/036968
§ 371 (c)(1),
(2) Date: Dec. 2, 2020

(87) PCT Pub. No.: WO2019/241516
PCT Pub. Date: Dec. 19, 2019

(65) Prior Publication Data
US 2021/0220054 A1    Jul. 22, 2021

Related U.S. Application Data

(60) Provisional application No. 62/684,605, filed on Jun. 13, 2018.

(51) Int. Cl.
*A61B 34/10* (2016.01)
*A61B 90/00* (2016.01)

(52) U.S. Cl.
CPC .............. *A61B 34/10* (2016.02); *A61B 90/36* (2016.02); *A61B 2034/102* (2016.02); *A61B 2034/105* (2016.02); *A61B 2090/3762* (2016.02)

(58) Field of Classification Search
CPC ... A61B 34/10; A61B 90/36; A61B 2034/102; A61B 2034/105; A61B 2090/3762; A61B 2034/104
See application file for complete search history.

(56) References Cited

U.S. PATENT DOCUMENTS 9,233,001 B2 *  1/2016  Miles ..................... A61B 34/10
9,795,500 B2 * 10/2017  Ingimundarson ..... A61F 5/0102
(Continued)

FOREIGN PATENT DOCUMENTS

CN    107847278 A  *  3/2018  ........... A61B 5/0059
JP    2014531920 A  * 12/2014  ......... A61F 2/30756
(Continued)

OTHER PUBLICATIONS

Melhem et al., "EOS biplanar X-ray imaging: concept, developments, benefits and limitations", Epub Feb. 16, 2016.*
(Continued)

*Primary Examiner* — Kandasamy Thangavelu
(74) *Attorney, Agent, or Firm* — Leason Ellis LLP

(57) ABSTRACT

A computing device uses a plurality of images of arthroplasty to measure implant position. A virtual three-dimensional model is generated using at least some of the plurality of images. Moreover, the computing device configured in accordance with the present application simulates, as a function of the virtual three-dimensional model, movement
(Continued)

at the site. As a function of the simulating, the computing device determines occurrence, location and type of impingement, and identifies, using the determined location and type of the impingement, a plurality of surgical plans for treating the impingement, wherein each of the surgical plans has a respective degree of treatment effectiveness and a respective degree of invasiveness. Further, the computing device selects one of the surgical plans in accordance with the selected plan's predetermined respective degree of effectiveness and in accordance with the selected plan's predetermined respective degree of invasiveness.

20 Claims, 14 Drawing Sheets

(56) References Cited

U.S. PATENT DOCUMENTS

| | | | |
|---|---|---|---|
| 2015/0057756 | A1 | 2/2015 | Lang et al. |
| 2017/0042619 | A1* | 2/2017 | Brooks .................. A61B 34/10 |
| 2017/0086674 | A1* | 3/2017 | Keefer ................. A61B 5/4504 |
| 2017/0224495 | A1* | 8/2017 | Rogachefsky ............ A61F 2/30 |
| 2017/0312031 | A1* | 11/2017 | Amanatullah ......... A61B 34/10 |
| 2018/0161101 | A1* | 6/2018 | Barsoum ................ A61F 2/468 |

FOREIGN PATENT DOCUMENTS

| | | | | |
|---|---|---|---|---|
| JP | 2015531661 A | * | 11/2015 | ............ G16Z 99/00 |
| WO | 2015089118 A1 | | 6/2015 | |
| WO | WO 2017106794 A1 | * | 6/2017 | ........... A61B 5/7242 |
| WO | WO 2018/067966 | | 4/2018 | |

OTHER PUBLICATIONS

GB Search Report in GB Application No. GB2212930.8, dated Sep. 14, 2022 (3 pages).
Parvizi J, Picinic E, Sharkey PF. Revision total hip arthroplasty for instability: surgical techniques and principles. J Bone Joint Surg Am. May 2008;90(5):1134-1142.
Philippot R, Adam P, Reckhaus M, et al. Prevention of dislocation in total hip revision surgery using a dual mobility design. Orthop Traumatol Surg Res. Aug. 4, 2009;95(6):407-413. doi:10.1016/j.otsr.2009.04.016.
Guo L, Yang Y, An B, et al. Risk factors for dislocation after revision total hip arthroplasty: A systematic review and meta-analysis. Int J Surg Lond Engl. Feb. 2017;38:123-129. doi:10.1016/j.ijsu.2016.12.122.
Bozic KJ, Kurtz SM, Lau E, Ong K, Vail TP, Berry DJ. The Epidemiology of Revision Total Hip Arthroplasty in the United States. J Bone Jt Surg. Jan. 2009;91(1):128-133. doi:10.2106/JBJS.H.00155.
Blom AW, Rogers M, Taylor AH, Pattison G, Whitehouse S, Bannister GC. Dislocation Following Total Hip Replacement: The Avon Orthopaedic Centre Experience. Ann R Coll Surg Engl. Nov. 2008;90(8):658-662. doi:10.1308/003588408X318156.
Sariali E, Lazennec JY, Khiami F, Catonne Y. Mathematical evaluation of jumping distance in total hip arthroplasty. Acta Orthop. Jun. 2009;80(3):277-282. doi:10.3109/17453670902988378.
Berry DJ, von Knoch M, Schleck CD, Harmsen WS. Effect of femoral head diameter and operative approach on risk of dislocation after primary total hip arthroplasty. J Bone Joint Surg Am. Nov. 2005;87(11):2456-2463. doi:10.2106/JBJS.D.02860.
Howie DW, Holubowycz OT, Middleton R, Large Articulation Study Group. Large femoral heads decrease the incidence of dislocation after total hip arthroplasty: a randomized controlled trial. J Bone Joint Surg Am. Jun. 2012;94(12):1095-1102. doi:10.2106/JBJS.K.00570.
Williams JT, Ragland PS, Clarke S. Constrained components for the unstable hip following total hip arthroplasty: a literature review. Int Orthop. Jun. 2007;31(3):273-277. doi:10.1007/s00264-006-0191-y.
Charlwood AP, Thompson NW, Thompson NS, Beverland DE, Nixon JR. Recurrent hip arthroplasy dislocation: Good outcome after cup augmentation in 20 patients followed for 2 years. Acta Orthop Scand. Oct. 2002;73(5):502-505. doi:10.1080/000164702321022758.
Ganz R, Parvizi J, Beck M, Leunig M, Nötzli H, Siebenrock KA. Femoroacetabular impingement: a cause for osteoarthritis of the hip. Clin Orthop. Dec. 2003;(417):112-120. doi:10.1097/01.blo.0000096804.78689.c2.
Beck M, Kalhor M, Leunig M, Ganz R. Hip morphology influences the pattern of damage to the acetabular cartilage: femoroacetabular impingement as a cause of early osteoarthritis of the hip. J Bone Joint Surg Br. Jul. 2005;87(7):1012-1018. doi:10.1302/0301-620X.87B7.15203.
Hetsroni I, Larson CM, Dela Torre K, Zbeda RM, Magennis E, Kelly BT. Anterior inferior iliac spine deformity as an extra-articular source for hip impingement: a series of 10 patients treated with arthroscopic decompression. Arthrosc J Arthrosc Relat Surg Off Publ Arthrosc Assoc N Am Int Arthrosc Assoc. Nov. 2012;28(11):1644-1653. doi:10.1016/j.arthro.2012.05.882.
Hetsroni I, Poultsides L, Bedi A, Larson CM, Kelly BT. Anterior inferior iliac spine morphology correlates with hip range of motion: a classification system and dynamic model. Clin Orthop. Aug. 2013;471(8):2497-2503. doi:10.1007/s11999-013-2847-4.
Esposito CI, Walter WL, Roques A, et al. Wear in alumina-on-alumina ceramic total hip replacements: a retrieval analysis of edge loading. J Bone Joint Surg Br. Jul. 2012;94(7):901-907. doi:10.1302/0301-620X.94B7.29115.
Lazennec JY, Brusson A, Rousseau MA. Lumbar-pelvic-femoral balance on sitting and standing lateral radiographs. Orthop Traumatol Surg Res OTSR. Feb. 2013;99(1 Suppl):S87-103. doi:10.1016/j.otsr.2012.12.003.
Esposito CI, Miller TT, Kim HJ, et al. Does Degenerative Lumbar Spine Disease Influence Femoroacetabular Flexion in Patients Undergoing Total Hip Arthroplasty? Clin Orthop. Aug. 2016;474(8):1788-1797. doi:10.1007/s11999-016-4787-2.
Berry DJ, Knoch M von, Schleck CD, Harmsen SW. The Cumulative Long-term Risk of Dislocation After Primary Charnley Total Hip Arthroplasy. J Bone Jt Surg-Am Vol. Jan. 2004;86A(1):9-14.
Eftekhar NS. Dislocation and instability complicating low friction arthroplasty of the hip joint. Clin Orthop. Nov.-Dec. 1976;(121):120-125.
Ekelund A, Rydell N, Nilsson OS. Total hip arthroplasty in patients 80 years of age and older. Clin Orthop. May 29, 1990;(281):101-106.
Alberton GM, High WA, Morrey BF. Dislocation after revision total hip arthroplasty : an analysis of risk factors and treatment options. J Bone Joint Surg Am. Oct. 2002;84-A(10):1788-1792.
Daly PJ, Morrey BF. Operative correction of an unstable total hip arthroplasty. J Bone Jt Surg. Oct. 1992;74(9):1334-1343.
Carter AH, Sheehan EC, Mortazavi SMJ, Purtill JJ, Sharkey PF, Parvizi J. Revision for recurrent instability: what are the predictors of failure? J Arthroplasty. Sep. 2011;26(6 Suppl):46-52. doi:10.1016/j.arth.2011.03.021.
Kaplan SJ, Thomas WH, Poss R. Trochanteric advancement for recurrent dislocation after total hip arthroplasty. J Arthroplasty. Jun. 1987;2(2):119-124. doi:10.1016/S0883-5403(87)80018-9.
McGann WA, Welch RB. Treatment of the unstable total hip arthroplasty using modularity, soft tissue, and allograft reconstruction. J Arthroplasty. Dec. 2001;16(8 Suppl 1):19-23. doi:10.1054/arth.2001.29137.
Dyrkacz RMR, Brandt J-M, Ojo OA, Turgeon TR, Wyss UP. The Influence of Head Size on Corrosion and Fretting Behaviour at the Head-Neck Interface of Artificial Hip Joints. J Arthroplasty. Jun. 2013;28(6):1036-1040. doi:10.1016/j.arth.2012.10.017.
Muratoglu OK, Bragdon CR, O'Connor D, et al. Larger diameter femoral heads used in conjunction with a highly cross-linked ultra-high molecular weight polyethylene: a new concept. J Arthroplasty. Dec. 2001;16(8 Suppl 1):24-30.

(56) References Cited

OTHER PUBLICATIONS

Malik A, Maheshwari A, Dorr LD. Impingement with total hip replacement. J Bone Joint Surg Am. Aug. 2007;89(8):1832-1842. doi:10.2106/JBJS.F.01313.
Toomey SD, Hopper RH, McAuley JP, Engh C a. Modular component exchange for treatment of recurrent dislocation of a total hip replacement in selected patients. J Bone Joint Surg Am. Oct. 2001;83-A(10):1529-1533.
Goldstein WM, Gleason TF, Kopplin M, Branson JJ. Prevalence of dislocation after total hip arthroplasty through a posterolateral approach with partial capsulotomy and capsulorrhaphy. J Bone Joint Surg Am. Oct. 2001;83-A Suppl(Pt 1):2-7.
Amstutz HC, Le Duff MJ, Beaule PE. Prevention and treatment of dislocation after total hip replacement using large diameter balls. Clin Orthop. Dec. 2004;(429):108-116.
Barrack RL. Dislocation after total hip arthroplasty: implant design and orientation. J Am Acad Orthop Surg. Mar.-Apr. 2003;11(2):89-99. doi:10.5435/00124635-200303000-00003.
Padgett DE, Lipman J, Robie B, Nestor BJ. Influence of total hip design on dislocation: A computer model and clinical analysis. In: Clinical Orthopaedics and Related Research. Jun. 2006:48-52. doi:10.1097/01.blo.0000218748.30236.40.
Barrack RL, Butler R a, Laster DR, Andrews P. Stem design and dislocation after revision total hip arthroplasty: clinical results and computer modeling. J Arthroplasty. Dec. 2001;16(8 Suppl 1):8-12. doi:aarth01608b0008 [pii].
Brien WW, Salvati EA, Wright TM, Burstein AH. Dislocation following THA: Comparison of two acetabular component designs. Orthopedics. Aug. 1993;16(8):869-872.
McCollum DE, Gray WJ. Dislocation after total hip arthroplasty. Causes and prevention. Clin Orthop. Dec. 1990;(261):159-170. doi:10.1097/00003086-199012000-00019.
Siebenrock KA, Kalbermatten DF, Ganz R. Effect of pelvic tilt on acetabular retroversion: a study of pelves from cadavers. Clin Orthop. Feb. 2003;(407):241-248.
Ranawat CS, Maynard MJ. Modern techniques of cemented total hip arthroplasty. Tech Orthop. Sep. 1991;6(3):17-25.
Burstein G, Yoon P, Saleh KJ. Component Removal in Revision Total Hip Arthroplasty. Clin Orthop. Mar. 2004;420:48-54.
Lazennec JY, Riwan A, Gravez F, et al. Hip spine relationships: application to total hip arthroplasty. Hip Int J Clin Exp Res Hip Pathol Ther. Jan. 1, 2007;17 Suppl 5:S91-104.
Esposito CI, Carroll KM, Sculco PK, Padgett DE, Jerabek SA, Mayman DJ. Total Hip Arthroplasty Patients With Fixed Spinopelvic Alignment Are at Higher Risk of Hip Dislocation. J Arthroplasty. Dec. 2017. doi:10.1016/j.arth.2017.12.005.
Pellicci PM, Bostrom M, Poss R. Posterior approach to total hip replacement using enhanced posterior soft tissue repair. Clin Orthop. Oct. 1998;(355):224-228.

\* cited by examiner

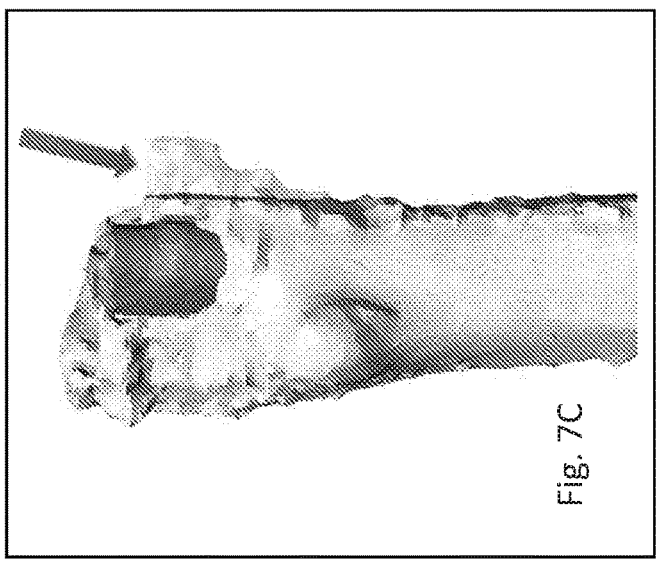
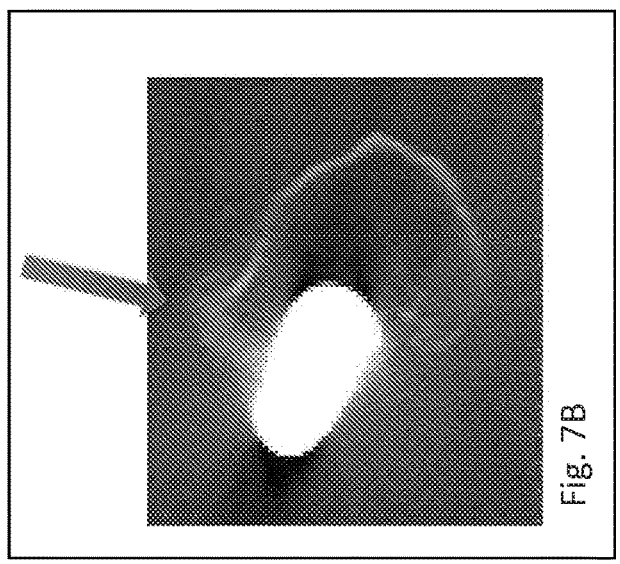
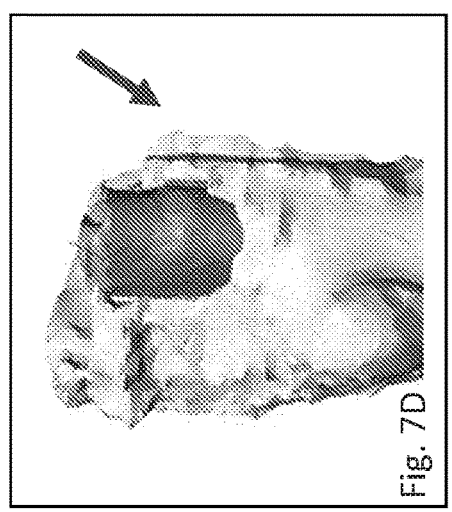
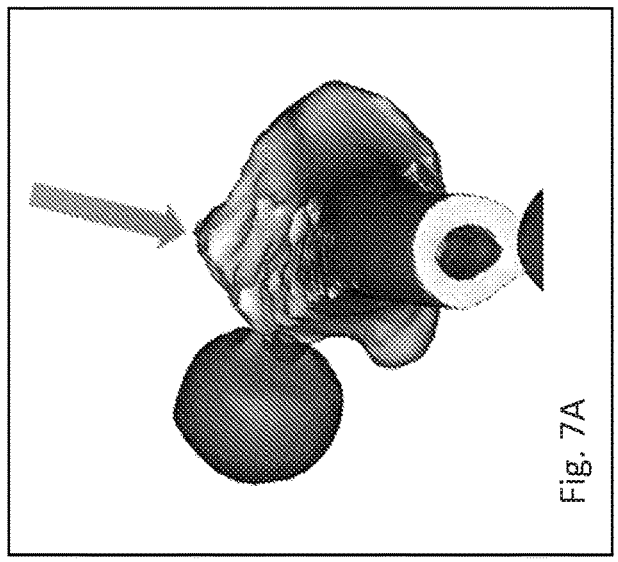
Fig. 7C
Fig. 7B
Fig. 7D
Fig. 7A

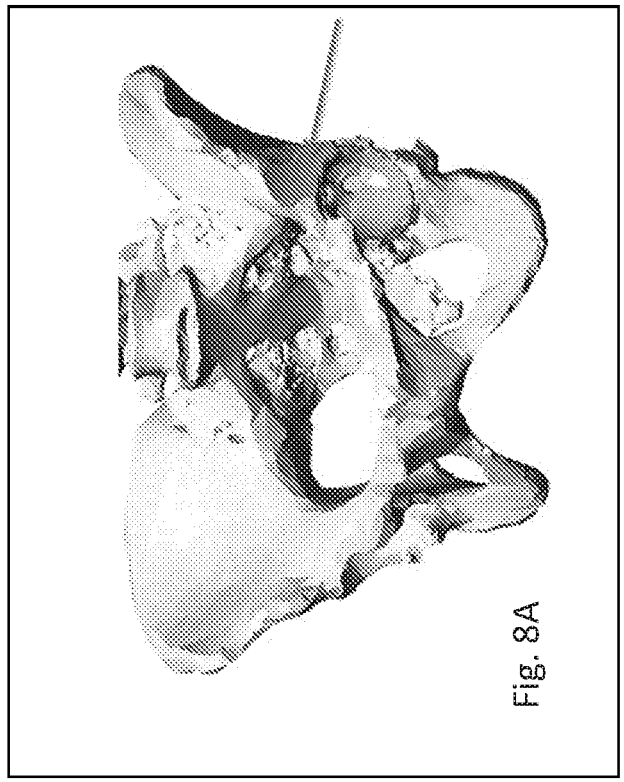
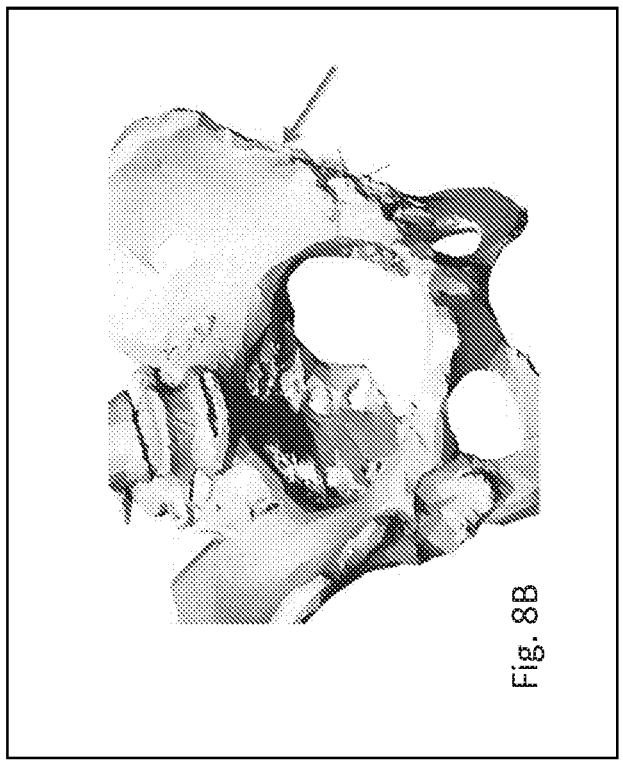
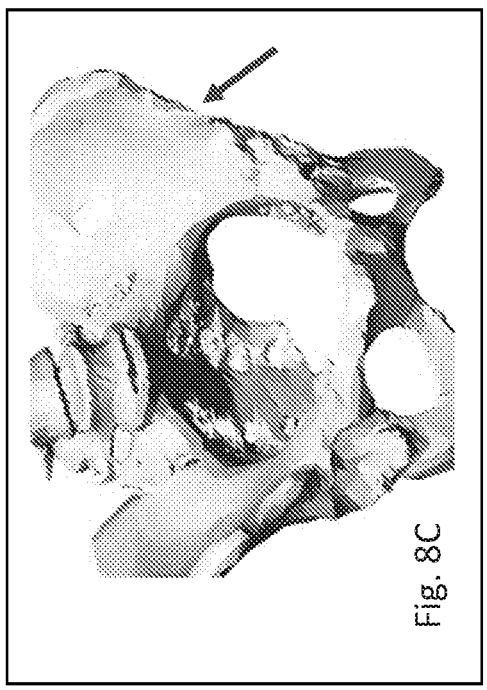
Fig. 8A
Fig. 8B
Fig. 8C

EVALUATION OF INSTABILITY USING IMAGING AND MODELING FOLLOWING ARTHROPLASTY

CROSS REFERENCE TO RELATED APPLICATION

This application is a U.S. National Phase Application under 35 U.S.C. § 371 of International Patent Application No. PCT/US2019/036968, filed Jun. 13, 2019, which claims priority to and the benefit of U.S. patent application Ser. No. 62/684,605 filed Jun. 13, 2018, each of which is incorporated by reference as if expressly set forth in their respective entirety herein.

FIELD OF THE INVENTION

The present disclosure relates, generally, to electronic medical systems and methods, and, more particularly, to providing a treatment plan as a function of virtual modeling and simulations.

BACKGROUND

Instability of a joint, such as subluxation and dislocation, continues to be among complications that can follow arthroplasty, such as total hip arthroplasty (THA). Instability often occurs during the early and late postoperative period. Reported rates of dislocation, for example, range from 0.1% to 9% following primary THA and 5% to 30% after revision THA. Singular episodes of instability may be successfully treated with reinforcement of hip precautions, provided components are properly aligned and hip mechanics can be or have been restored.

Specific instances of instability can be caused by bone-on-bone impingement, acetabular implant-on-bone impingement, femoral implant-on-bone impingement, and acetabular and femoral implant-on-implant impingement just to name a few. Various surgical options for treatment of instability post THA include, but are not limited to, bone resection and/or component revision, acetabular implant revision and resection of osteophytes/bony prominence (such as on the proximal femur), femoral implant and resection of prominent anterior superior iliac spine (AIIS), and acetabular and/or femoral implant revision (e.g., increasing femoral head size). Surgical options can include correcting malpositioned components, using an elevated liner, a dual mobility construct, or a constrained liner. It is recognized that each surgical option carries possible drawbacks, such as an increased wear of the liner and increased taper corrosion, which need to be considered when considering corresponding treatment benefits. For example, although constrained or tripolar cup designs have reduced postoperative dislocation rates, the mechanical failure of the locking ring or dissociation of a cemented liner is problematic. Surgical intervention to improve stability is not always effective, and it is believed that the risk of further hip dislocations following revision surgery is in the range of 21% to 30%.

The effectiveness of treatment strategies for instability vary. Further various treatment strategies have different degrees of invasiveness. In many instances, conservative treatments may not be effective for patients who dislocate following arthroplasty and surgical intervention is indicated. In view of these and other concerns, the present application provides the following systems and methods.

SUMMARY

A system and method are provided for preoperatively evaluating impingement following arthroplasty and providing a surgical plan as a function of virtual modeling and simulation. In one or more implementations, a computing device configured by executing code stored on non-transitory processor readable media analyzes a plurality of images of a site of the arthroplasty to measure implant position and to assess a person's functional orientation. Further, the computing device generates a virtual three-dimensional model using at least some of the plurality of images. Moreover, the computing device configured in accordance with the present application simulates, as a function of the virtual three-dimensional model, movement at the site. As a function of the simulating, the computing device determines occurrence, location and type of impingement, and identifies, using the determined location and type of the impingement, a plurality of surgical plans for treating the impingement. Each of the surgical plans has a respective degree of treatment effectiveness and a respective degree of invasiveness. Further, the computing device selects one of the surgical plans in accordance with the selected plan's predetermined respective degree of effectiveness and in accordance with the selected plan's predetermined respective degree of invasiveness.

Further, in one or more implementations, the images can include at least one image of a first type and at least one image of a second type, wherein the first type can include computed tomography scans and the second type can include planar radiographic images.

Still further, in one or more implementations, the planar radiographic images include EOS biplanar radiographic X-rays.

In one or more implementations of the present application, the computing device can be configured to align after generating the virtual three-dimensional model, at least two of the images by translating and/or rotating at least one of the images.

In one or more implementations of the present application, at least one of the plurality of images is of a patient in a standing position and at least one of the images is of a patient in a sitting position.

Moreover, in one or more implementations of the present application, measuring the implant position includes measuring an acetabular cup orientation and a femoral implant orientation.

Still further, in one or more implementations of the present application, the movement includes flexion, adduction, and external rotation. The movement can include flexion to 90° followed by external rotation.

Moreover, in one or more implementations of the present application, the simulated movement is based at least in part on a likelihood of dislocation.

Moreover, in one or more implementations of the present application, the impingement includes at least one of: bone-on-bone impingement, implant-on-implant impingement, and implant on bone impingement.

A respective treatment effectiveness can include at least one of improved range of motion and a decreased likelihood of dislocation. Further, the surgical plans can include: revising a femoral head size; reorienting a malpositioned component; providing an i) elevated liner, or ii) a constrained liner; or a dual mobility bearing; component revision; boney resection; and repairing soft tissue.

Furthermore, in in one or more implementations of the present application, measuring the implant position includes measuring anteversion.

These and other aspects, features, and advantages can be appreciated from the accompanying description of certain embodiments of the invention and the accompanying drawing figures and claims.

BRIEF DESCRIPTION OF THE DRAWINGS

Various features, aspects and advantages of the invention can be appreciated from the following detailed description and the accompanying drawing figures, in which:

FIGS. 3-10 illustrate example virtual three-dimensional models of bone, implants and treatment options that are generated from advanced imaging techniques, modeling and simulation in accordance with implementations of the present application.

DETAILED DESCRIPTION OF THE EMBODIMENTS

Figure 1:
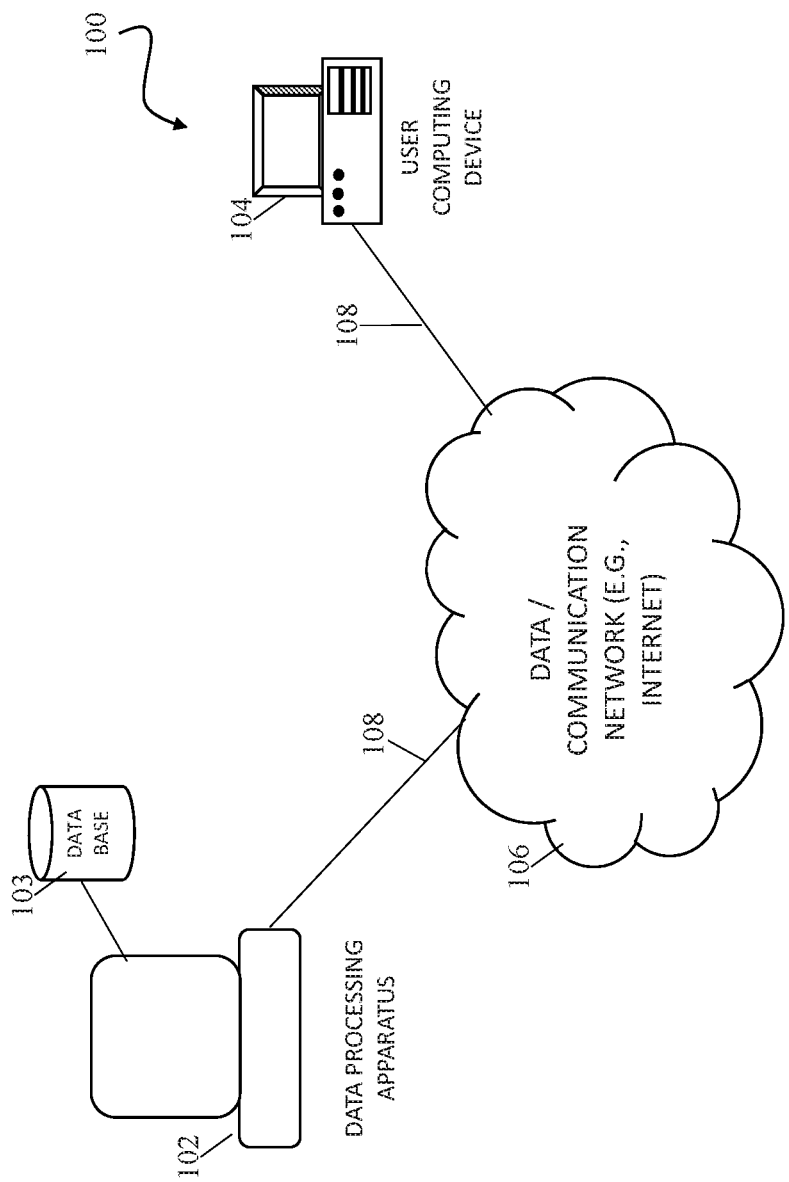
FIG. 1 is a block diagram illustrating an example implementation of the present application and that represents an association of a plurality of devices and the flow of information associated with the devices.

By way of overview and introduction, the present application includes computer-based systems, methods and interfaces for evaluating (joint) instability following arthroplasty, including impingement and dislocation, and corresponding treatment options, including surgical plans in accordance with the evaluation. Automated imaging and modeling techniques are used to simulate activity and instability, and for identifying one or more mechanisms that can be responsible for instability following THA. For example, a computing device configured with imaging and modeling software applications can simulate activity, such as joint movement, and identify a precise moment when impingement occurs. A computing device configured in accordance with the teachings herein can analyze the respective cause(s) and identify a plurality of treatment options as a function of the virtual modeling and simulation.

In one or more implementations of the present application, computed tomography scans and planar radiographic images of a patient can be taken and/or accessed, and used by one or more computing devices configured with programming code to measure implant position and to assess a patient's functional orientation, such as in connection with particular positions the patient is in and/or activities the patient is engaged in. The orientation can be, for example, the patient in a sitting position and in a standing position, or bending over to lift an object. Thereafter, the images can be mapped (e.g., combined) and virtual three-dimensional models can be generated and used to simulate patient activity that can result in instability, such as impingement. Further, the location and type of instability can be identified as well.

Information associated with impingement involving bone, implant, or soft tissues can be identified and/or generated by a computing device configured in accordance with the teachings herein. The information can be used by the computing device to evaluate various surgical options for treating instability after THA. Modeling hip kinematics can elucidate the underlying impingement mechanism responsible for eventual hip dislocation. For example, specifics regarding implant position, hip range of motion are used by one or more computing devices to identify locations of impingement. For example, limited hip range of motion can be attributed to bone or implant impingement. Alternatively, limited hip range of motion can reveal no cause attributed to bone and implants alone, suggesting soft tissue causes of dislocation. The type and location of impingement is usable by one or more computing devices to identify a plurality of strategies (e.g., surgical plans) for treating hip instability.

Thus, in one or more implementations of the present application, simulating activity and instability via virtual modeling enables a computing device to identify a plurality of treatment plans that are available in respective contexts. Each of the respective treatment plans, thereafter, can be evaluated at least in terms of effectiveness and invasiveness, and one preferred surgical plan can be selected based on the evaluation. For example, a computing device can be configured to make a determination, as a function of modeling, that a prominent anterior superior iliac spine limits hip range of motion, and activity results in impingement and posterior dislocation. Following kinematic modeling and simulation procedures shown and described herein, a selected treatment option involving resecting the hypertrophic anterior inferior iliac spine (AIIS) is identified to result in improved hip range of motion and reduced likelihood of dislocation. AIIS deformity can be an extra-articular source for hip impingement, and hypertrophy of the AIIS can limit hip range of motion. Further, such resection is determined to be the least invasive treatment option among a plurality of options that provide similar degrees of effectiveness.

Accordingly, preoperative kinematic analysis of THA can be useful for identifying impingement mechanisms that contribute to limited range of motion. Further, such analysis is useful to provide treatment options for instability, as well as for planning surgical treatment and improving patient outcomes. For example, the simulation and modeling technology provided by the present application identifies a cause and suggests a new alignment target for a malpositioned component, and to identify a particular intraoperative execution treatment option therefor.

Accordingly, a plurality of algorithmic techniques are shown and described herein that can be applied in one or more computer-based processes to identify types of impingement in THA. Such techniques can operate to balance particular treatment options, such as whether component revision or boney resection would be most suitable to improve hip range of motion and reduce or eliminate impingement. Modeling techniques include simulating movement and anatomical responses, such as when impingement occurs (e.g., bone-on-bone or implant-on-implant) during movement.

The present application includes systems and methods that address difficulties associated with developing a treatment plan, such as a surgical plan, for various forms of instability such as dislocation, particularly in cases in which the causes of instability are unclear. As known in the art, impingement can result in a dynamic process which is difficult to identify or define based on clinical evaluations or plain radiographs, and which may be driven by multiple factors including hip offset, implant design, component position, and boney geometry. In accordance with the teachings herein, information regarding the underlying dislocation mechanism is provided in one or more virtual contexts that enables a computing device to identify the condition and cause, and to provide an appropriate treatment (e.g., surgical).

Referring to the drawings, in which like reference numerals refer to like elements, FIG. 1 is a block diagram illustrating an example implementation of the present application and that represents an association of a plurality of devices and the flow 108 of information associated with the devices. In the example shown in FIG. 1, various computing devices 102 and 104 are shown, each capable of executing desktop and/or mobile computing device web browser application(s) including INTERNET EXPLORER, CHROME, FIREFOX, and other (e.g., SAFARI, OPERA). In addition to standard web browser application functionality, user information can be gathered via Push Notifications, and information can be retrieved from a computing device using a "REST" interface. Various mobile devices running different operating systems are shown, including IOS, ANDROID and other (e.g., PALM, WINDOWS or other mobile device operating system).

In the example shown in FIG. 1, one or more data processing apparatuses 102 is operatively coupled to one or more user computing device(s) 104. Devices 102/104 can be respectively operated by one or more healthcare providers and associated staff, medical specialists and/or consumers. Healthcare providers can include, for example, physicians, physician assistants, nurses, therapists and/or other providers of healthcare services. Data processing apparatus 102 and/or user computing device 104 can be operable to access and/or store various information on database(s) 103 including, for example, medical image information, personal or identifying information about a user/patient, information identifying a respective computing device and/or software operating thereon, user activity, medical history, profession, preferences, a current location, or the like.

In addition, certain data can be treated in one or more ways before being stored or used, so that personally identifiable information is not displayed. For example, a person's identification number can be used to retrieve detailed information about a user, and which can be transmitted to a healthcare professional. The healthcare professional (or the specific employee or agent of the professional) may not be provided with personally identifiable information about the patient. In this way, a user's anonymity can be preserved, for example to maintain expectations of anonymity. Also illustrated in FIG. 1 is a network 106, which can be configured as a local area network (LAN), wide area network (WAN), Peer-to-Peer network ("P2P"), Multi-Peer network, the Internet, one or more telephony networks or a combination thereof, that is operable to connect data processing apparatus 102 and/or devices. Though many of the examples and implementations shown and described herein relate to product and/or service recommendations, many other forms of content can be provided and/or delivered by system 100.

Figure 2:
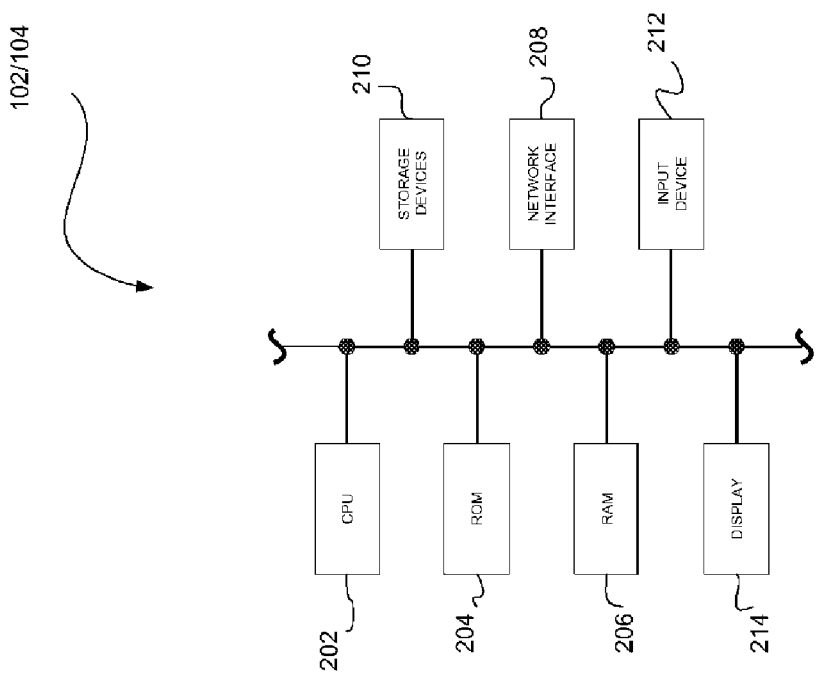
FIG. 2 is a block diagram that illustrates functional elements of one or more of data processing apparatus and/or user computing device.
Figure 3C:
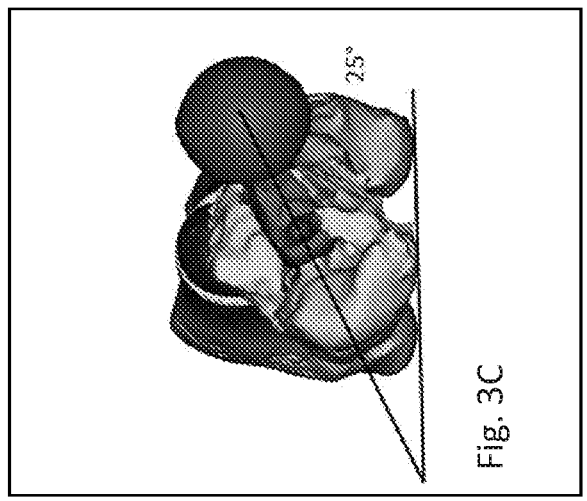
Figure 3B:
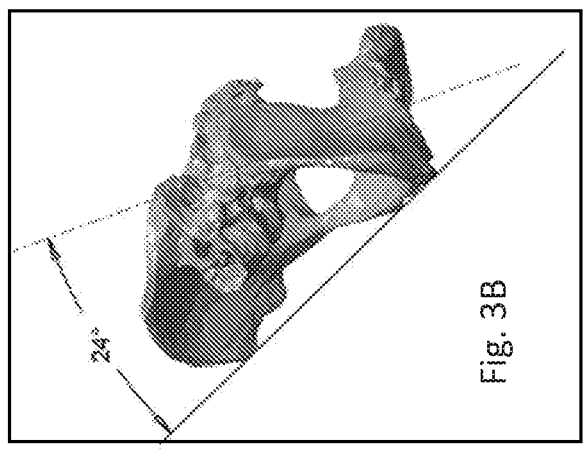
Figure 3A:
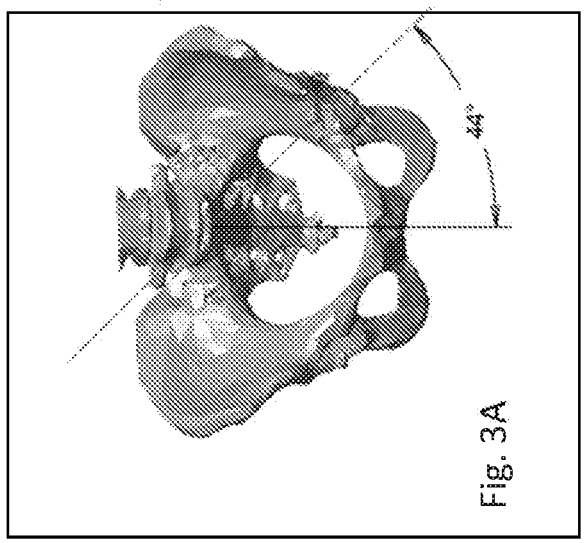

FIG. 2 is a block diagram that illustrates functional elements of one or more of data processing apparatus 102 or computing device 104 and preferably include one or more central processing units (CPU) 202 used to execute software code in order to control operations, including of data processing apparatus 102, read only memory (ROM) 204, random access memory (RAM) 206, one or more network interfaces 208 to transmit and receive data to and from other computing devices across a communication network, storage devices 210 such as a hard disk drive, solid state drive, floppy disk drive, tape drive, CD-ROM or DVD drive for storing program code, databases and application code, one or more input devices 212 such as a keyboard, mouse, track ball and the like, and a display 214.

The various components of devices 102 and/or 104 need not be physically contained within the same chassis or even located in a single location. For example, storage device 210 can be located at a site which is remote from the remaining elements of computing devices 102 and/or 104, and can even be connected to CPU 202 across communication network 106 via network interface 208.

The functional elements shown in FIG. 2 (designated by reference numbers 202-214) are preferably of the same categories of functional elements preferably present in computing device 102 and/or 104. However, not all elements need be present, for example, storage devices in the case of PDAs, and the capacities of the various elements are arranged to accommodate expected user demand. For example, CPU 202 in computing device 104 can be of a smaller capacity than CPU 202 as present in data processing apparatus 102. Similarly, it is likely that data processing apparatus 102 will include storage devices 210 of a much higher capacity than storage devices 210 present in computing device 104. Of course, one of ordinary skill in the art will understand that the capacities of the functional elements can be adjusted as needed.

The nature of the present application is such that one skilled in the art of writing computer executed code (software) can implement the described functions using one or more or a combination of a popular computer programming language including but not limited to C++, JAVA, ACTIVEX, HTML, XML, ASP, SOAP, IOS, OBJECTIVE C, ANDROID, TORR and various web application development environments.

As used herein, references to displaying data on computing device 104 refer to the process of communicating data to the computing device 104 across communication network 106 and processing the data such that the data can be viewed on the user computing device 104 display 214 using a web browser, custom application or the like. The display screens on computing devices 102/104 present areas within system 100 such that a user can proceed from area to area within the system 100 by selecting a desired link. Therefore, each user's experience with system 100 will be based on the order with which (s)he progresses through the display screens. In other words, because the system is not completely hierarchical in its arrangement of display screens, users can proceed from area to area without the need to "backtrack" through a series of display screens. For that reason and unless stated otherwise, the following discussion is not intended to represent any sequential operation steps, but rather the discussion of the components of system 100.

Although the present application is described by way of example herein in terms of a web-based system using web browsers, custom applications and a web site server (data processing apparatus 102), and with mobile computing devices, system 100 is not limited to that particular configuration. It is contemplated that system 100 can be arranged such that computing device 104 can communicate with, and display data received from, data processing apparatus 102 using any known communication and display method, for example, using a non-Internet browser Windows viewer coupled with a local area network protocol such as the Internetwork Packet Exchange (IPX). It is further contemplated that any suitable operating system can be used on computing device 104, for example, WINDOWS 3.X, WINDOWS 95, WINDOWS 98, WINDOWS 2000, WINDOWS CE, WINDOWS NT, WINDOWS XP, WINDOWS VISTA-WINDOWS 7, WINDOWS 8, MAC OS, OSX, LINUX, IOS, ANDROID and any suitable PDA or palm computer operating system.

As used herein, the terms "function" or "module" refer to hardware, firmware, or software in combination with hardware and/or firmware for implementing features described herein. In the hardware sense, a module can be a functional hardware unit designed for use with other components or modules. For example, a module may be implemented using discrete electronic components, or it can form a portion of an entire electronic circuit such as an Application Specific Integrated Circuit (ASIC). Numerous other possibilities exist, and those of ordinary skill in the art will appreciate that the system can also be implemented as a combination of hardware and software modules. In the software sense, a module may be implemented as logic executing in a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, Perl, or Python. It will be appreciated that software modules may be callable from other modules or from themselves, and/or may be invoked in response to detected events or interrupts. Software instructions may be embedded in firmware. Moreover, the modules described herein can be implemented as software modules, but may be represented in hardware or firmware. Generally, the modules described herein refer to logical modules that may be combined with other modules or divided into sub-modules despite their physical organization or storage.

With reference to FIGS. 3-10, three-dimensional models of bone, implants and treatment options that are generated from advanced imaging techniques, modeling and simulation are illustrated as being exemplary of the teachings of the present invention. Anatomical images can be of a first type and of a second, different type. For example, three-dimensional computed tomography (CT) scans are taken of a patient following THA and more particularly, are taken after an event, such as a joint dislocation, has occurred. The CT scans can be taken with the patient in a supine position and can include the pelvis from the anterior superior iliac spines to the proximal one third of the femur, as well as the distal femur in order to enable measurement of femoral torsion. Additionally, frontal and lateral plane two-dimensional radiographs, such as low-dose radiation X-rays, can be taken of the pelvis while the patient is in a standing position and/or a sitting position. An example low-dose radiation system images is provided by EOS Imaging.

In accordance with an example implementation, CT scans can, thereafter, be segmented, such as via MIMICS simulation software provided by Materialise NV. Segmenting the CT scans provides for respective image files, for example of the pelvis, proximal femur, distal femur, femoral component and acetabular component, and can be exported to one or more individual digital image file formats, such as stereolithography (".stl") files. One or more data processing apparatuses 102 can analyze respective images (e.g., three .stl image files shown in FIGS. 3A, 3B, and 3C) of bones (e.g., a patient's pelvis) and implants, including to measure positions and/or orientations of an acetabular and femoral implant that were placed during THA. For example, anteversion and femoral angles are measured. The measurement in FIG. 3A (44°) is acetabular inclination, the measurement in FIG. 3B (24°) is acetabular anteversion, and the measurement in FIG. 3C (25°) is femoral anteversion. Bone-on-bone impingement occurs often in hips with decreased anteversion of the femoral stem (<5 degrees) and short neck length. Data processing apparatus 102 can, accordingly, direct that anterior superior aspect of the femur to be excised.

Figure 4C:
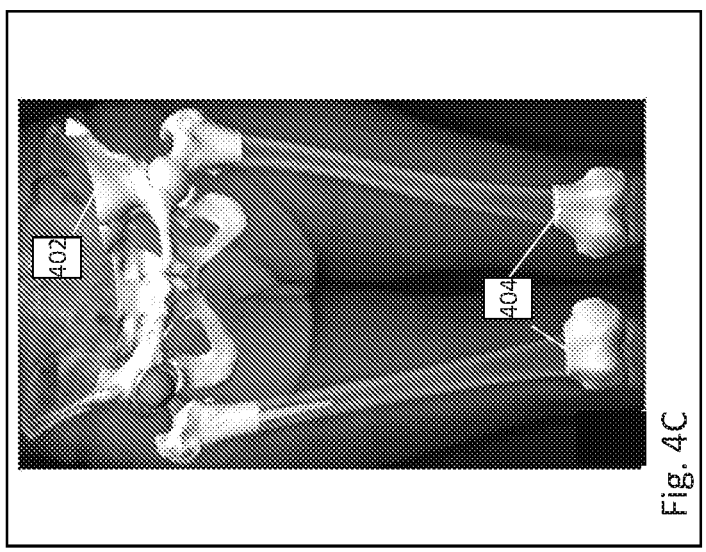
Figure 4B:
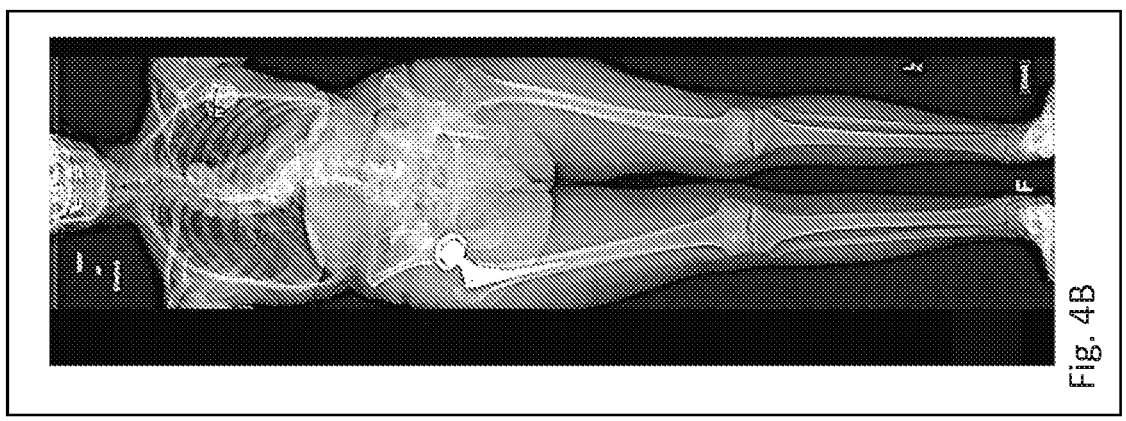
Figure 4A:
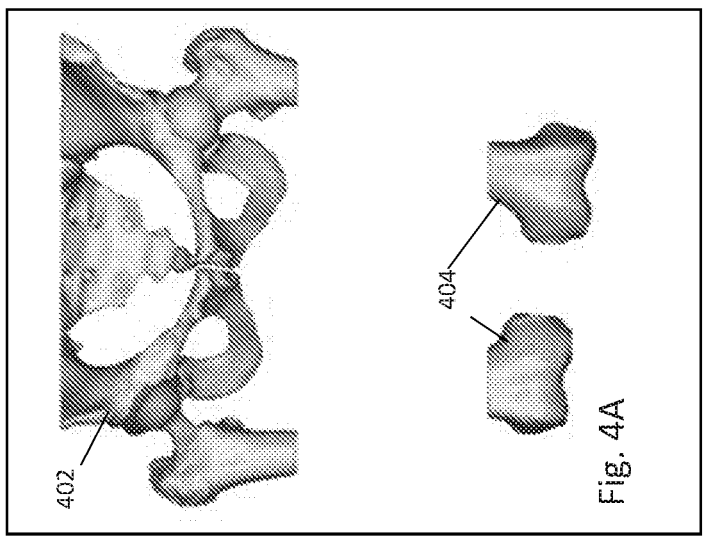

FIGS. 4A, 4B, and 4C illustrate example images associated with mapping/modeling functionality provided in connection with one or more implementations. In the examples shown in FIGS. 4A, 4B, and 4C, image files of one or more CT scans (FIG. 4A) include the pelvis region and implant 402 of a patient's pelvis and implant (e.g. acetabulum implant), and the lower condylar portion 404 of the femur is shown. FIG. 4B illustrates an example two-dimensional radiograph of the patient following THA. FIG. 4C illustrates the .stl files (virtual 3D model) of the CT scan(s) of FIG. 4A (including portions 402 and 404) mapped or otherwise combined with the radiograph of FIG. 4B, thereby combining the different image types together and more particularly, combining a 3D model (generated from CT scan) with a 2D image. In the example shown in FIG. 4C, the .stl files are aligned with the two-dimensional radiograph, such as by automatically translating and/or rotating portions 402 and/or 402 by data processing apparatus 102. More particularly, the 3D model (based on the CT scan) of FIG. 4A is mapped onto and combined with the 2D radiograph of FIG. 4B and the 3D image is manipulated (e.g., translating and/or rotating the virtual 3D model) so that target anatomical landmarks (e.g., elements 402 and/or 404) in FIG. 4A (3D image) assume at least substantially the same position and/or orientation as the same anatomical landmarks in the 2D image (FIG. 4B). In this sense, the combined image of FIG. 4C depicts a functional position of these anatomical landmarks since the patient is in a functional position (e.g., standing position) in FIG. 4B. In other words, a virtual 3D model(s) is generated from the CT scan(s) and is then combined with the 2D image(s) of the same anatomical landmarks and then the virtual 3D model is translated and/or rotated until the target landmarks in the virtual 3D model are in at least substantially the same spatial positions as the same anatomical landmarks in the 2D image (i.e., they overlap). Once this desired degree of alignment is achieved, the virtual simulations can be performed as described herein.

Figure 5B:
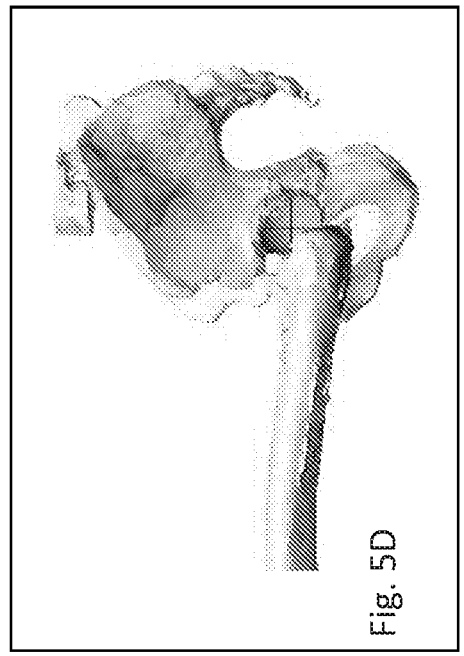
Figure 5D:
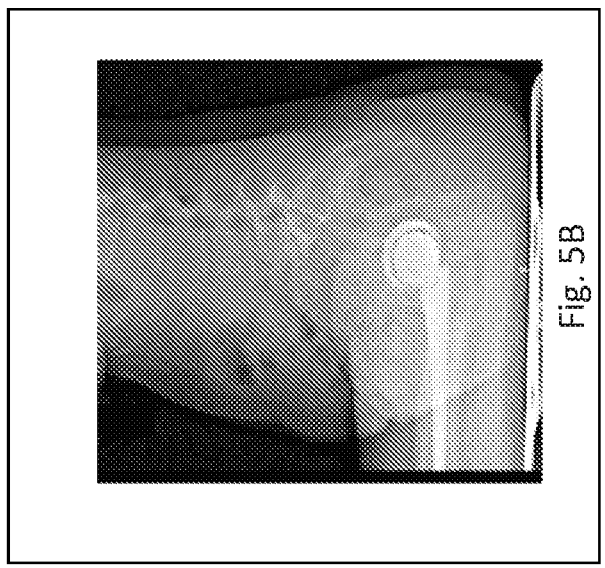
Figure 5A:
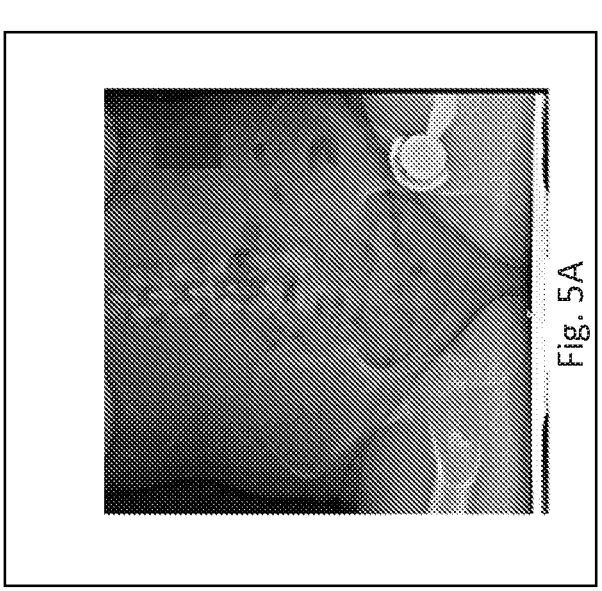
Figure 5C:
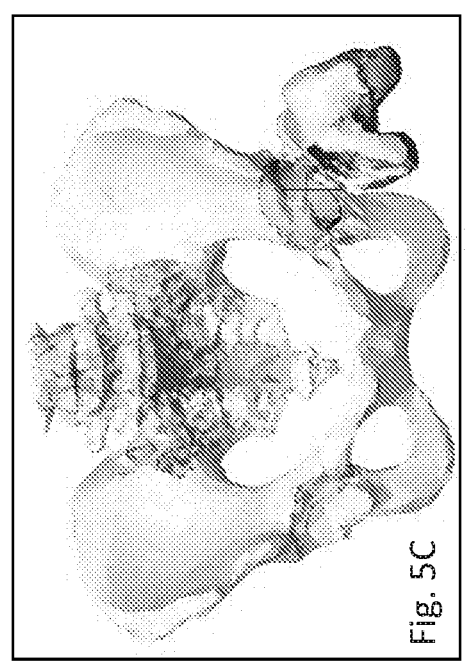

FIGS. 5A and 5B illustrate additional example two-dimensional radiographs of a patient's pelvic region while in a sitting position, and illustrating the THA implants. FIGS. 5C and 5D illustrate corresponding views from one or more CT scans via .stl file(s), and are capable of being rotated and/or translated to align images for mapping and modeling. The images in FIGS. 5C and 5D have been rotated to match the planar images above them, for example, from being in an extended position to a flexed position. Mapping the respective images enables the data processing apparatus 102 to make accurate preoperative assessments of implant position and impingement, including as dependent on the functional orientation of the pelvis and the femur during activities of daily living and provocative positions that can cause instability. The data processing apparatus 102 can identify a difference in pelvic tilt and femoral rotation in the CT scan compared to standing or seated position (see, for example, FIGS. 4A-4C and FIGS. 5A-5D).

Figure 5F:
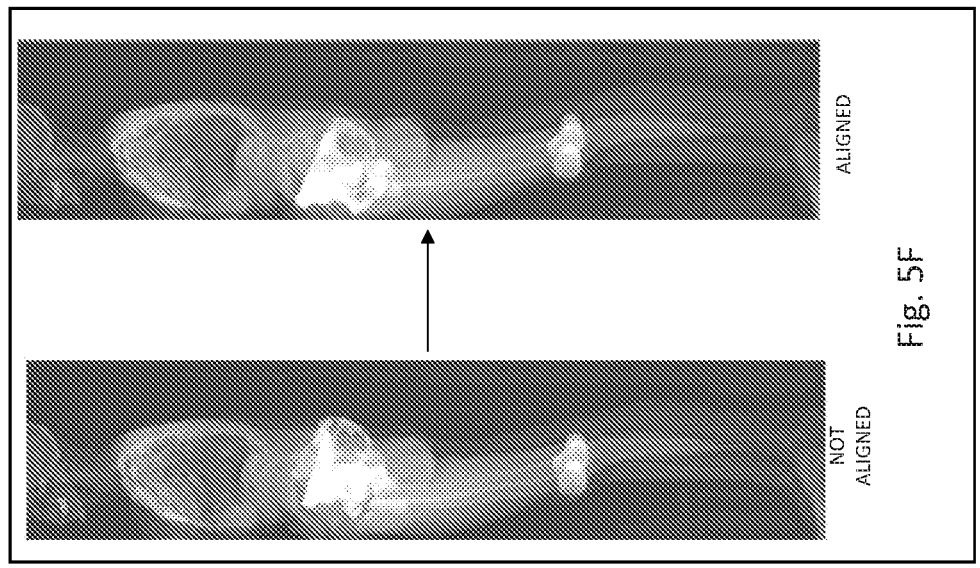
Figure 5E:
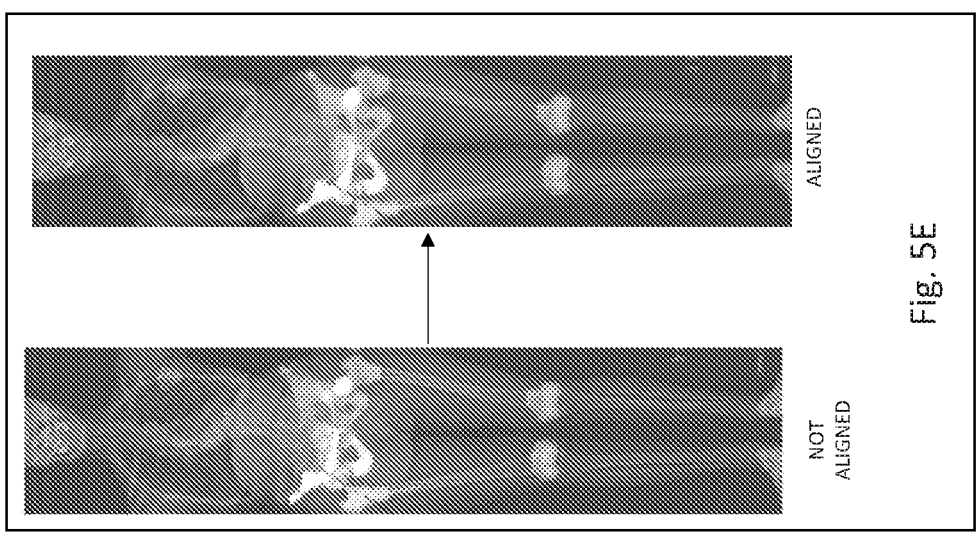

FIGS. 5E and 5F illustrate processes associated with aligning virtual three-dimensional models with 2D images in accordance with two respective views: a forward view (FIG. 5E) and a lateral (90° offset from the forward view) view (FIG. 5F). It is recognized that biplanar images are useful for alignment. Data processing apparatus 102, for example, can identify certain alignment information as a function of a first (e.g., frontal) view (FIG. 5E). That information can be augmented as a function of a second (e.g., lateral) view (FIG. 5F), which improves processes for aligning the virtual three-dimensional model with the 2D image(s). Alignment of the virtual three-dimensional model can occur by translating and/or rotating (the 3D model) in the sagittal, coronal, and axial planes, as appropriate and until desired alignment is achieved.

Accurately identifying the negative impact on range of motion that pelvic tilt and corresponding impingement have enables data processing apparatus 102 to identify treatment options, such as those that take into consideration spine mechanics. For example, spine disease can limit a patient's ability to accommodate postural changes through the lumbar spine, which alters hip kinematics and increases the risk of hip dislocation. The modeling and simulating practices of the present application, including as implemented via mapping the virtual 3D model derived from the CT scans to two-dimensional radiographic X-rays, enables the data processing apparatus 102 to account for such factors.

Using the mapped CT scans (virtual 3D model) and two-dimensional radiographs, multibody dynamic modeling is provided to enable data processing apparatus 102 to simulate activities and/or measure component orientation. In this way, instability including impingement and/or dislocation can be represented virtually, including in response to activity such as a patient moving from a low chair or bending over to reach an object. For example, the virtual 3D model is moved over a range of motion as part of a virtual simulation until an impingement event occurs or until the end of the range of motion is completed with no impingement detected. As shown and described herein, the specific type and mechanics of impingement can be identified and a corresponding treatment plan provided.

Figure 6:
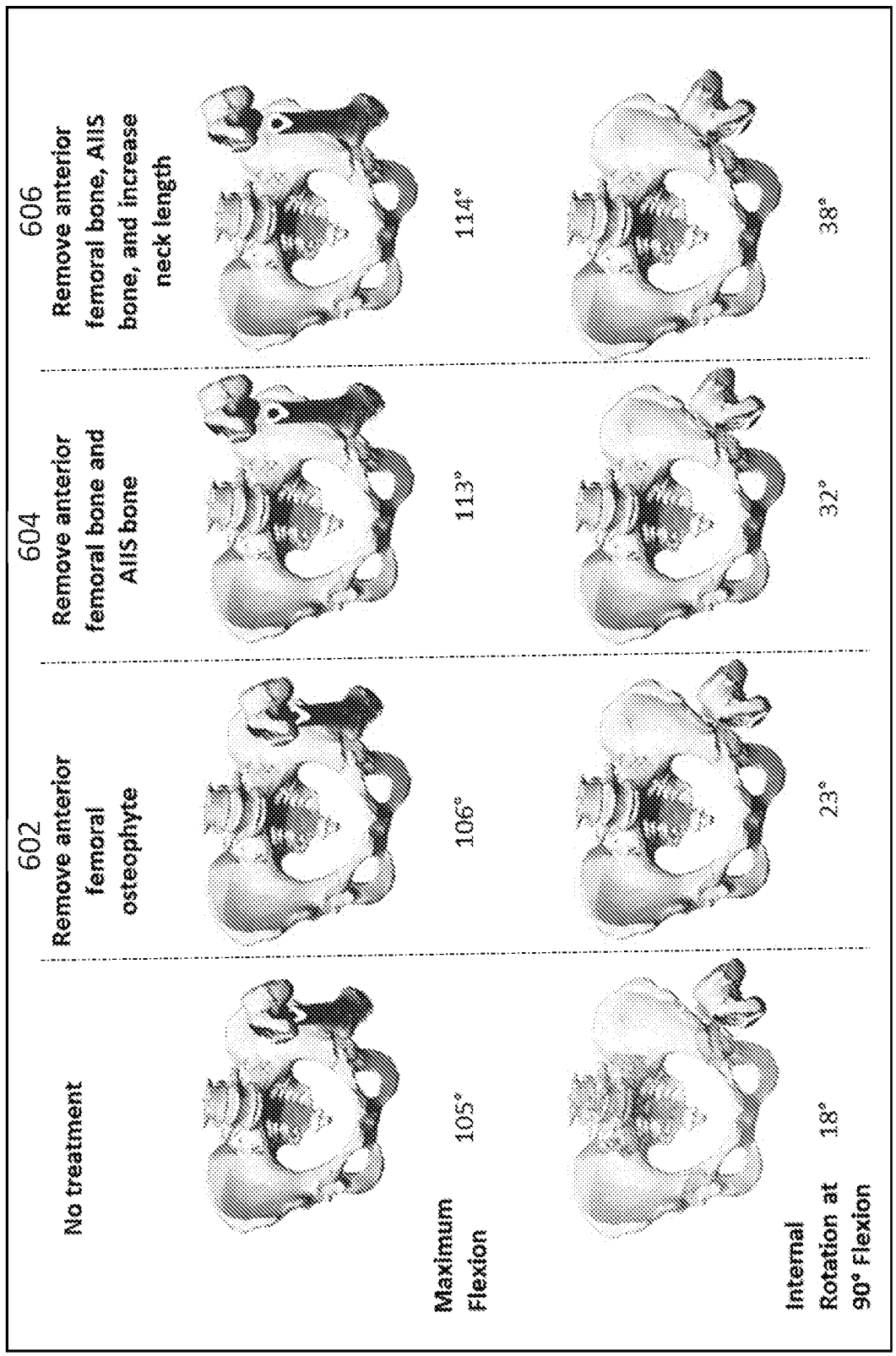

FIG. 6 illustrates an example treatment options for post-THA treatment, ranging from least invasive to most invasive. In one or more implementations of the present application, patient activity is simulated to determine when and where impingement can occur. Image files can be imported into multibody dynamic modeling software, such as SIM-WISE 4D by Design Simulation Technologies. Accordingly, a plurality of treatment options and corresponding range of motion analyses are supported. The options include i) no treatment, ii) removal of anterior femoral osteophyte (602), iii) removal of anterior femoral bone and anterior superior iliac spine bone (604), and iv) removal of anterior femoral osteophyte, removal of anterior femoral bone and anterior superior iliac spine bone, and lengthening the hip (606). In the example shown in FIG. 6, virtual posterior dislocation occurs with flexion, adduction and internal rotation, and the data processing apparatus 102 calculates range of motion to maximum flexion (with neutral abduction and neutral rotation) and maximum internal rotation at 90 degrees of flexion (with neutral abduction) prior to the point of impingement. In this example model, the virtual pelvis remains fixed in position, and the femur is rotated about the center of the femoral head in the motions described above. Predetermined threshold values were for acceptable or limited range of motion include maximum hip flexion, internal rotation at 90° flexion and external rotation at 20° extension with mean hip flexion to be 118°±6°, mean internal rotation to be 38°±3°, and mean external rotation to be 29°±5°. Two standard deviations below the means were 106° flexion, 32° internal rotation and 19° external rotation, which were the values used to identify limited hip range of motion.

Continuing with reference to FIG. 6, data apparatus 102 identifies the location and type of impingement, such as bone-on-bone or implant-on-implant as a function of virtual modeling, and uses that information to develop a preoperative plan for improving range of motion. Surgical options for improving range of motion include, but are not limited to, reorientation of the acetabular component, reorientation of the femoral component, revising the femoral head to increase hip offset or removal of impinging bone. These different surgical plans respectively improve range of motion associated with bone-on-bone impingement between the AIIS and the anterior aspect of the proximal femur. In the example shown in FIG. 6, modeling technology had previously shown and described evidence of a prominent AIIS and a proximal femoral osteophyte, and an analysis performed by data processing apparatus 102 evaluated respective treatment options. Further data processing apparatus 102 evaluated the effectiveness as well as the invasiveness of the respective options, and provided a selection and recommendation of a preoperative plan that includes at least removal of anterior femoral osteophyte (602, 604, 606) (see, for example, FIGS. 7A-7D). Further, the preoperative plan includes at least removal of AIIS bone (604, 606) (see, for example, 8A-8C). In the example shown in FIG. 6, the model provided by data processing apparatus 102 identifies that option 604 is the preferred option, given the respective effectiveness and invasiveness of plans 602, 604, and 606. Data apparatus 102 identifies that option 604 improves the patient's range of motion from 105° flexion to 113° flexion and from 18° internal rotation to 32° internal rotation (FIG. 6). As part of the patient's assessment, data processing apparatus 102 determines that surgical option 606, which increases neck length an additional 4 mm and includes a high offset head or lateralized liner, would only result in improved hip range of motion by 1° (i.e. from 113° to 114°) flexion and internal rotation would be improved only by 6° (i.e. from 32° to 38°) (see, for example, FIG. 6). The other treatment option 602 identified in FIG. 6, removal of anterior femoral osteophyte, would only result in improved range of motion by 1° (i.e. from 105° to 106°) flexion and internal rotation would be only improved by 5° (i.e. from 18° to 23°). Accordingly, the conclusion is that neither option 602 or option 606 provide sufficient effectiveness and/or is too invasive to be considered a recommended course of treatment by data processing apparatus 102.

Figure 9:

In addition to identifying respective treatment options, data processing apparatus 102 can be further configured to simulate results of surgical procedures and to provide virtual representations thereof. For example, and with reference to FIGS. 7C and 7D, data processing apparatus 102 can simulate at least a portion of the treatment options 602, 604, 606 that includes removal of anterior femoral bone. FIG. 7C illustrates anterior femoral osteophyte that contributes to impingement. FIG. 7D illustrates a simulated removal of the anterior femoral osteophyte. Further, and with reference to FIGS. 8B and 8C, data processing apparatus 102 can simulate at least a portion of the treatment options 604, 606 that includes removal of AIIS bone. FIG. 8B illustrates AIIS osteophyte that contributes to impingement. FIG. 8C illustrates a simulated removal of AIIS osteophyte. In one or more implementations, simulations can identify degrees of bone removal, with particular indications in a graphical interface, such as when too much bone removal would result in compromising the ability to support an implant (not shown) or otherwise result in joint instability. Moreover, FIG. 9 illustrates a simulation provided by data apparatus 102 that includes lengthening femoral neck length, such as identified in treatment option 606. For some patients, lengthening of the femoral neck length can result in increased joint stability, thereby reducing the likelihood of joint dislocation. In the example shown, increasing the neck length moves the femur away from the pelvis which increases range of motion.

Figure 10:
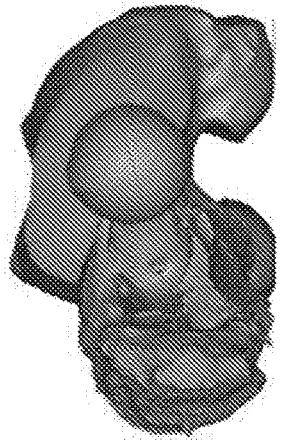
Figure 10:
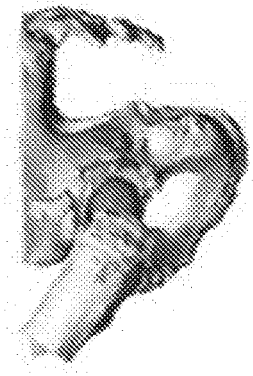
Figure 10:
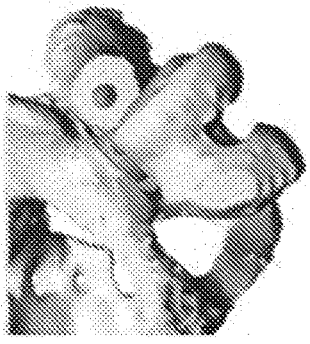
Figure 10:
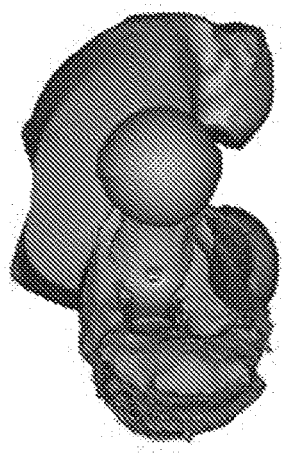
Figure 10:
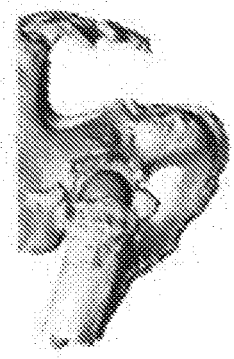
Figure 10:
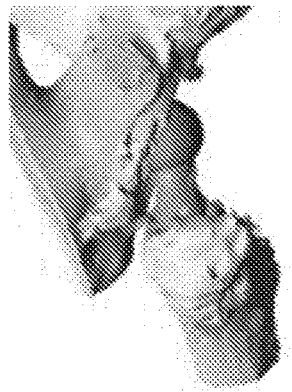

FIG. 10 illustrates another example of modeling and simulation of movement and instability in connection with an untreated unstable hip following THA. Further, respective modeling and simulation is provided following a selected, recommend treatment plan 1002 by data processing apparatus 102. For example, the untreated unstable hip has maximum range of motion values of 104° flexion and 18° internal rotation (at 90° flexion). The recommended treatment plan 1002 to revise the femoral component and increase femoral anteversion from 6° retroversion to 14° anteversion improves each of these respective values to 119° from 104° flexion and to 32° internal rotation (at 90° flexion) from 18°, which each represents a significant improvement in potential patient outcome.

Accordingly, treatment options to address THA instability by modeling and simulation show predicted improved range of motion in connection with respective treatment options. Furthermore, a selection of one of the plurality of treatment options is provided, in accordance with the respective effectiveness and invasiveness of each option.

Figure 11:
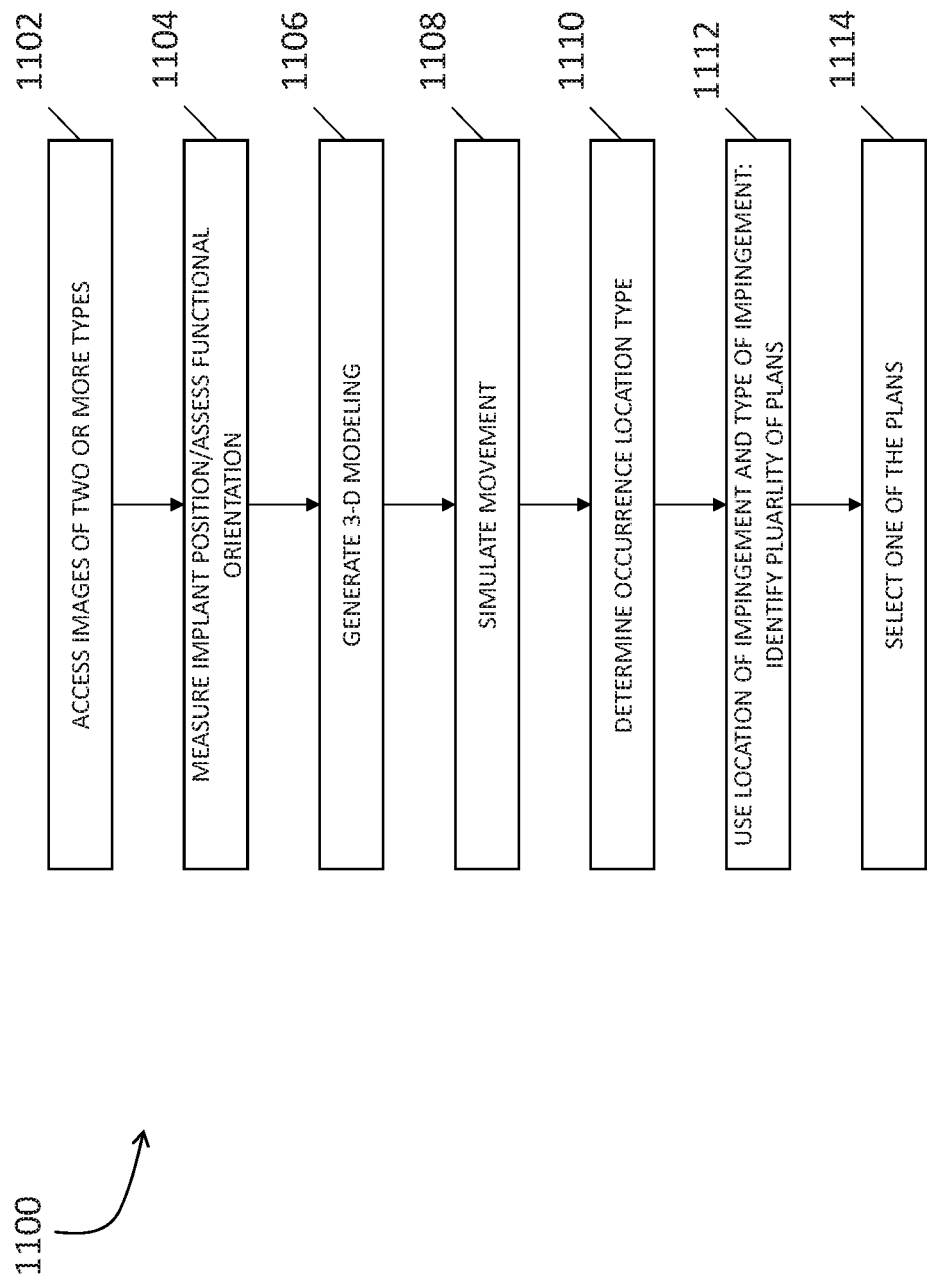
FIGS. 11-13 are flowcharts that illustrate example workflows in accordance with one or more implementations of the present application.

Turning now to FIG. 11, a flow diagram shows an example routine 1100 that illustrates a broad aspect of a method for automatically evaluating instability following arthroplasty. Further the flow diagram of FIG. 11 describes steps for providing a surgical plan as a function of virtual modeling and simulation, in accordance with one or more implementations of the present application. Among other objectives, the routine 1100 improves and optimizes preoperative planning, including by evaluating effectiveness and invasiveness of respective treatment options.

It is to be appreciated that several of the logical operations described herein are implemented as a sequence of computer-implemented acts or program modules running on one or more computing devices that are operatively connected (e.g., mobile computing device, server computing device) and/or as interconnected machine logic circuits or circuit modules within the system. Accordingly, the logical operations described herein are referred to variously as operations, steps, structural devices, acts and modules can be implemented in software, in firmware, in special purpose digital logic, and any combination thereof. It should also be appreciated that more or fewer operations can be performed than those shown in the figures and described herein. These operations can also be performed in a different order than those described herein.

Continuing with reference to FIG. 11, the process 1100 begins at step 1102, in which at least two types of medical images, such as conventional two-dimensional X-rays and CT scans, are accessed. The images can be accessed, for example, from database 103. At step 1104, one or more modules executed by or in conjunction with data processing apparatus 102 used the respective images to take measurements of implant position and/or orientation. At step 1106, data processing apparatus 102 generates three-dimensional modeling associated with at least some of the images, and at step 1108 simulates movement associated with activity. Thereafter, an occurrence of impingement is identified, including the type and location of impingement (step 1110). The location and type of impingement is used to identify a plurality of treatment plans, such as surgical interventions, to improve patient outcomes including with regard to range of motion (step 1112). At step 1114, one of the plurality of treatment options is selected that represents a maximum effectiveness in view of a respective degree of treatment invasiveness.

Figure 12:
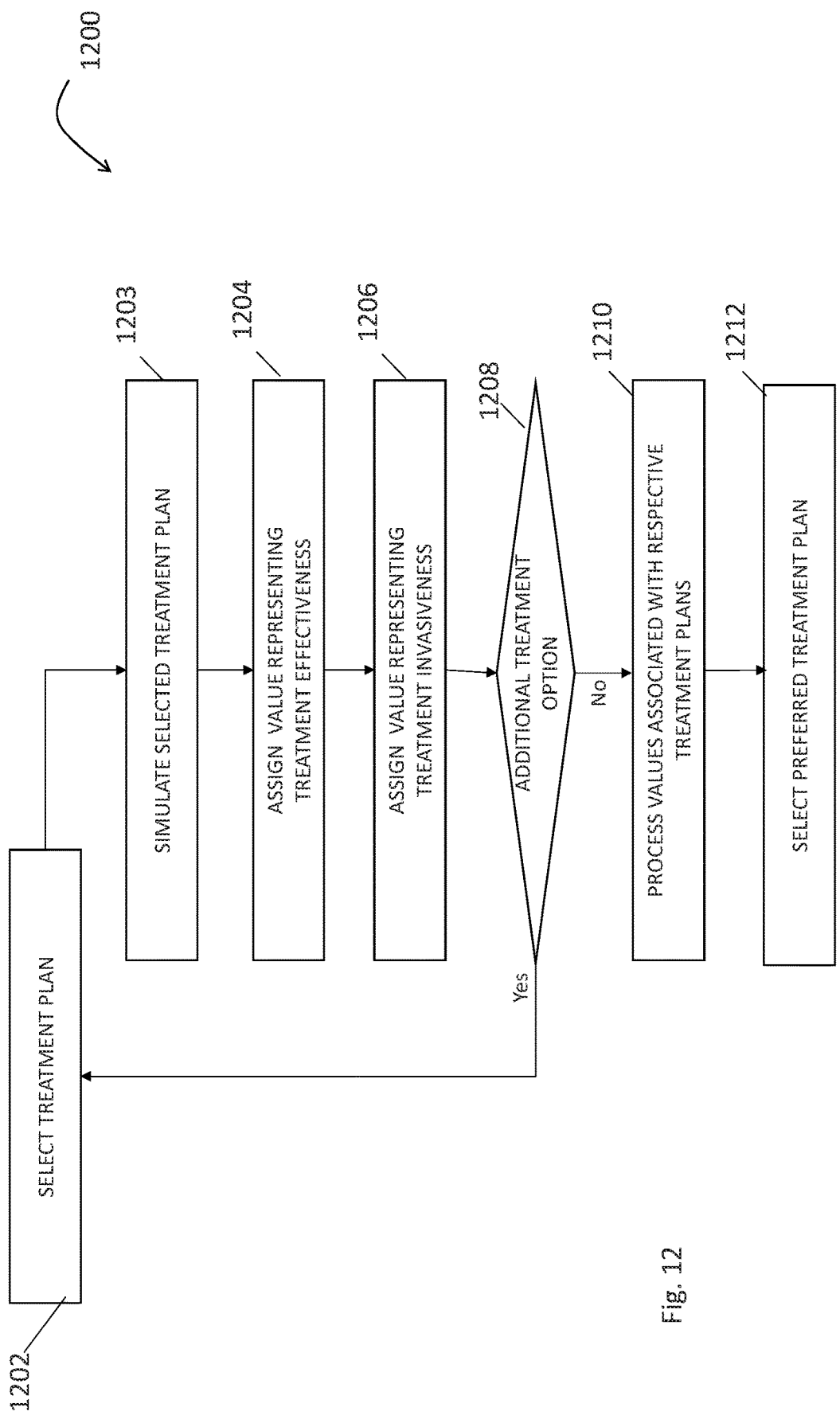

Referring now to FIG. 12, a flow diagram shows an example routine 1200 that illustrates a broad aspect of a method for automatically analyzing a plurality of treatment plans, and for selecting a preferred one of the plurality of treatment plans. The process 1200 begins at step 1202, and a selection of one of a plurality treatment plans, such as plans identified in step 1112 (FIG. 11), is made for further processing. At step 1203, one or more modules executed by or in association with data processing apparatus 102 simulate steps associated with the selected treatment plan. For example, and as illustrated in FIGS. 7C and 7D, and in FIGS. 8B and 8C, removal of a bone osteophyte is simulated. In addition, or in the alternative, a simulated range of motion following the procedure is measured up until the point of impingement. Alternatively, and in one or more implementations, one or more implant surfaces and/or one or more bone surfaces can be virtually modified. For example, data processing apparatus 102 automatically or via a user using one or more graphical screen controls provided in a user interface virtually modify the bone surface and then the simulated range of motion is measured up until the point of any impingement. For example, the acetabular bone can be virtually shaved at an impingement location as an attempt to increase the range of motion into a target acceptable range. In one embodiment, the software described herein can be configured such that the one or more points of impingement can be highlighted on the display screen. At step 1204, a value representing the effectiveness of the selected treatment option is assigned by data processing apparatus 102. At step 1206, an analysis of the respective invasiveness of the selected treatment option is made by data processing apparatus 102 and a value representing the invasiveness is assigned. Thereafter, a determination is made at step 1208 whether there is an additional treatment option that has not yet been processed. If the determination at step 1208 is affirmative, then the process branches back to step 1202 and another treatment plan is selected. If the determination at step 1208 is negative, then the process branches to step 1210 and the effectiveness and invasiveness values assigned for the respective treatment options are processed, thereby enabling data processing apparatus 102 to select one of the treatment plans that provides the maximal amount of effectiveness balanced with the degree of invasiveness of the respective treatment.

Figure 13:
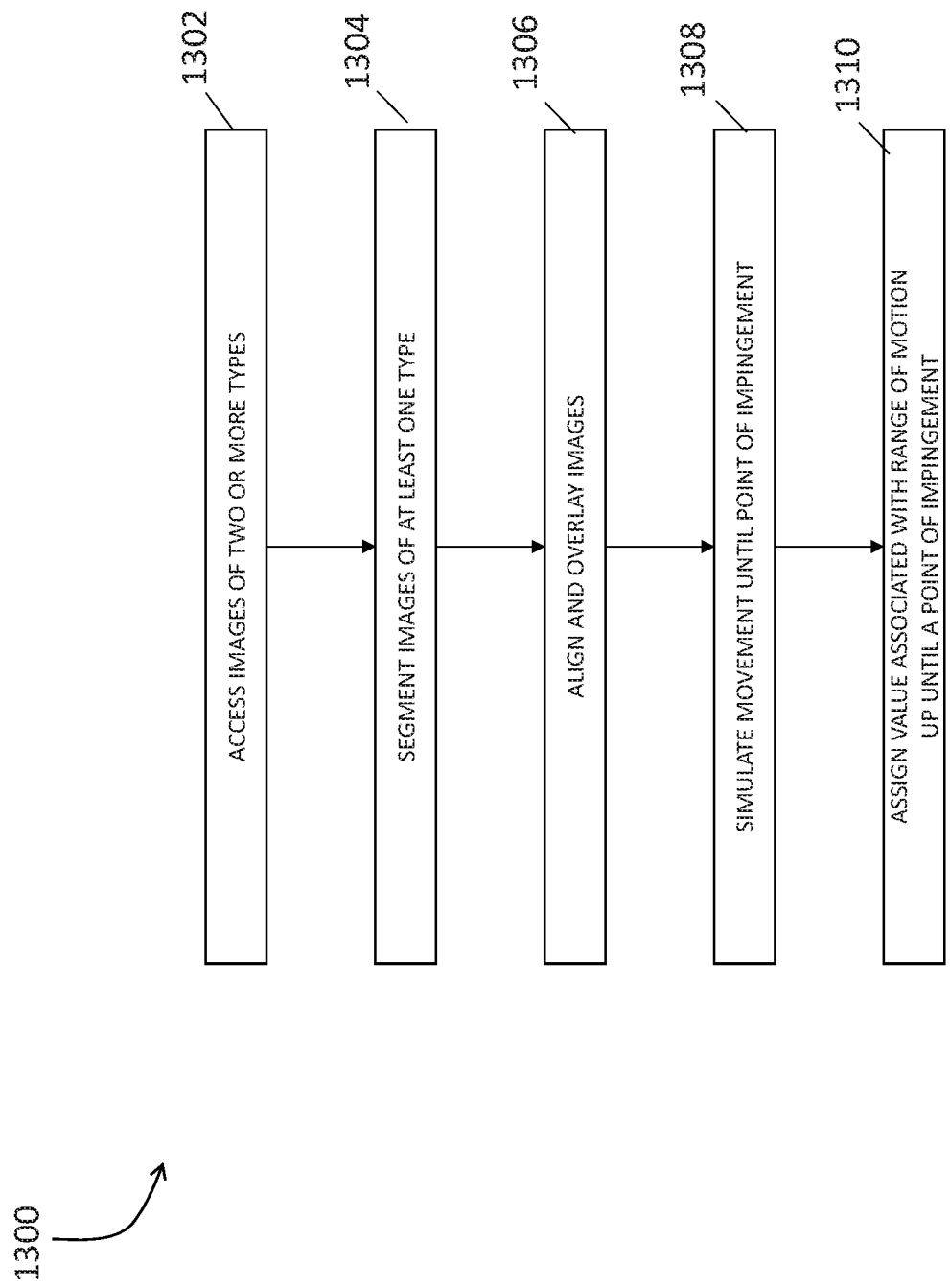

Referring now to FIG. 13, a flow diagram shows an example routine 1300 that illustrates a broad aspect of the method for automatically providing modeling and simulated movement in accordance with one or more implementations of the present application. At step 1302, images of at least two different types, such as conventional two-dimensional X-rays and CT scans, are accessed by data processing apparatus 102. At step 1304, at least some of the images, such as originating from CT scans, are segmented and one or more images are exported for modeling, movement simulation, and analyzing treatment options. At step 1306, at least one of the segmented images is aligned and overlaid with at least one of the other images, such as shown and described herein with reference to FIGS. 4A-4C. At step 1308, movement is simulated, including virtually flexing the patient's hip joint until impingement is virtually detected. At step 1310, a value is recorded that represents the respective range of motion, such as flexion, adduction, and rotation, just up to the point of impingement.

Thus, and as shown and described herein, the present application provides a computer-based algorithmic approach for treating hip instability after THA. The systems and methods of the present application address instability, including to identify and preclude impingement and dislocation after primary THA. More specifically, the preoperative systems and methods herein provide for extensive processing of images and information generated as a function of modeling and simulations. Such processing enables data processing apparatus 102 to identify treatment options and to assess the effectiveness and invasiveness of respective treatment options. Further, particular options and recommendations associated with specific treatments can be provided. Impingement modeling, for example, can show improved range of motion with component revision. Further, overlaying respective images ensures that the orientation of implants or the boney resections performed intraoperatively remain within an acceptable clinical range. In one or more instances, avoidance of constrained liners can be realized, which can be good for patients who have instability of unclear etiology or cognitive problems. Further, the teachings herein are useful to assess patients prone to anterior hip dislocations by virtually evaluating hip external rotation range of motion in extension. Further, optimal implant position or boney resections around native hips or THAs are usable to improve patient outcomes.

Much of the boney impingement that is directly observable as a function of the modeling systems and methods herein would otherwise be overlooked or missed by a THA surgeon. This is at least in part because prominent boney features, such as the AIIS, are not observable on conventional anteroposterior radiographs. Moreover, the present application improves the ability to identify misaligned THA implants, which can cause instability, high wear and poor hip range of motion. Thus, the modeling and simulation techniques of the present application identify the cause of limited motion and possible dislocation due to implant malalignment. Further still, new alignment targets can be provided to correct a malpositioned component as a function of virtual modeling and simulation of a preoperative plan. As noted herein, component revision is highly invasive and difficult, and alternative recommended treatment options provided by the present application may include revising a femoral component in one case, but not another, such as in case a simulated hip range of motion identifies no evidence of impingement following cup repositioning. In such case, therefore, the present application can operate to recommend a more conservative course of treatment involving resection of the AIIS and/or increase neck length to improve hip range of motion. Further, the present application can operate to recommend implanting a dual mobility bearing or elevated liner for improved hip stability in certain cases, but not others. The benefits provided herein include improved patient outcomes, as well as cost and time savings.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. Moreover, descriptions set forth herein provided, for example, by data processing apparatus 102 can be performed substantially automatically by modules executing by or in accordance with data processing apparatus 102, and/or as a function of user instructions received, such as in response to graphical screen controls provided in a user interface. In certain implementations, multitasking and parallel processing may be advantageous.

Although the foregoing has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed:

1. A computer-implemented method for preoperatively evaluating impingement following arthroplasty and providing a surgical plan based on computer-based modeling and simulation, the method comprising:
   accessing, by a computing device a plurality of images of a site of the arthroplasty, including a computed tomography scan of a person in a supine position and at least one planar radiographic image of the person in a sitting position or a standing position;
   generating, by the computing device using at least the computed tomography scan, -a virtual three-dimensional model of at least a bone of the person;
   translating and/or rotating the virtual three-dimensional model of at least the bone of the person to align the virtual three-dimensional model with at least the planar radiographic image of the person;
   simulating, by the computing device based on the virtual three-dimensional model, movement associated with the bone at the site of the arthroplasty;
   determining, by the computing device based on the simulating, occurrence, location and type of the impingement;
   identifying, by the computing device using the determined location and type of the impingement, a plurality of surgical plans for treating the impingement, wherein each of the surgical plans has a degree of treatment effectiveness and a degree of invasiveness; and
   selecting, by the computing device, one of the surgical plans in accordance with the selected plan's predetermined degree of effectiveness and predetermined degree of invasiveness.

2. The method of claim 1, wherein the planar radiographic images include EOS biplanar radiographic X-rays.

3. The method of claim 1, wherein the at least one planar radiographic image includes a plurality of planar radiographic images, and further wherein at least one of the planar radiographic images shows a front view 7 and at least one of the planar radiographic images shows a lateral view, and the aligning includes translating and/or rotating the virtual three-dimensional model of at least the bone of the person relative to at least one of the plurality of planar radiographic images of the person.

4. The method of claim 1, further comprising determining, by the computing device, implant position by measuring an acetabular cup orientation and a femoral implant orientation.

5. The method of claim 1, wherein the movement includes flexion.

6. The method of claim 1, wherein the movement includes flexion to 90° followed by internal rotation.

7. The method of claim 1, wherein the simulated movement is based at least in part on a likelihood of dislocation.

8. The method of claim 1, wherein the impingement includes at least one of:
bone-on-bone impingement, implant-on-implant impingement, and implant on bone impingement.

9. The method of claim 1, wherein the treatment effectiveness includes at least one of improved range of motion and a decreased likelihood of dislocation.

10. The method of claim 1, wherein the surgical plans include: revising a femoral head size; reorienting a malpositioned component; providing an i) elevated liner, or ii) a constrained liner; or a dual mobility bearing; component revision; boney resection; and repairing soft tissue.

11. The method of claim 1, wherein measuring the implant orientation includes measuring anteversion.

12. The method of claim 1, wherein the bone includes the person's femur, the person's pelvis, or the person's femur and the person's pelvis.

13. A computer-implemented method for preoperatively evaluating impingement following arthroplasty, the method comprising:
accessing, by a computing device, images of a site of the arthroplasty, wherein at least one of the images is a computed tomography scan of a person in a supine position and at least one of the images is a planar radiographic image of the person in a sitting position or a standing position;
generating, by the computing device using at least the computed tomography scan, a virtual three-dimensional model of at least a bone of the person;
aligning, by the computing device, the virtual three-dimensional model of at least the bone of the person with at least the planar radiographic image of the person by translating and/or rotating the virtual three-dimensional model of at least the bone of the person relative to the planar radiographic image of the person;
simulating, by the computing device based on virtual three-dimensional model, movement associated with the bone at the site of the arthroplasty;
determining, by the computing device based on the simulating, an occurrence of impingement, a location of the impingement and a type of the impingement; and
outputting, by the computing device, the determined type and location of the impingement.

14. The method of claim 13, wherein the biplanar radiographic images include EOS biplanar X-rays.

15. A system comprising a computing device executing a program of instructions stored on a computer readable medium to perform operations comprising:
accessing, by the computing device, a plurality of images of a site of the arthroplasty including at least one computed tomography scan of the person in a supine position and at least one planar radiographic image of the person in a sitting position or a standing position;
generating, by the computing device using at least the computed tomography scan, a virtual three-dimensional model of at least a bone of the person;
translating and/or rotating the virtual three-dimensional model of at least the bone of the person to align the virtual three-dimensional model with at least the planar radiographic image of the person;
simulating, by the computing device based on the virtual three-dimensional model, movement associated with the bone at the site of the arthroplasty;
determining, by the computing device based on the simulating, occurrence, location and type of the impingement;
identifying, by the computing device using the determined location and type of the impingement, a plurality of surgical plans for treating the impingement, wherein each of the surgical plans has a degree of treatment effectiveness and a degree of invasiveness; and
selecting one of the surgical plans in accordance with the selected plan's predetermined degree of effectiveness and predetermined degree of invasiveness.

16. The system of claim 15, wherein the impingement includes at least one of: bone-on-bone impingement, implant-on-implant impingement, and implant-on-bone impingement.

17. The system of claim 15, wherein the bone includes the person's femur, the person's pelvis, or the person's femur and the person's pelvis.

18. The system of claim 15, wherein the at least one planar radiographic image includes a plurality of planar radiographic images, and further wherein at least one of the planar radiographic images shows a front view and at least one of the radiographic images shows a lateral view, and further wherein the aligning includes translating and/or rotating the virtual three-dimensional model of at least the bone of the person relative to at least one of the planar radiographic images of the person.

19. The system of claim 15, wherein the treatment effectiveness includes at least one of improved range of motion and a decreased likelihood of dislocation.

20. The system of claim 15, wherein the surgical plans include: revising a femoral head size; reorienting a malpositioned component; providing an i) elevated liner, or ii) a constrained liner; or a dual mobility bearing; component revision; boney resection; and repairing soft tissue.

* * * * *